United States Patent [19]

Trouet et al.

[11] Patent Number: 4,870,162
[45] Date of Patent: Sep. 26, 1989

[54] CONJUGATES OF VINBLASTINE, A PROCESS FOR THEIR PREPARATION AND THEIR USE IN THERAPY

[75] Inventors: Andre B. L. Trouet, Winksele; Kandukuri S. Bushana, Rosieres; Jean A. A. Hannart, Dion-Valmont; Jean-Paul Dejonghe, Wavre, all of Belgium

[73] Assignee: Omnichem, Belgium

[21] Appl. No.: 854,909

[22] Filed: Apr. 23, 1986

Related U.S. Application Data

[63] Continuation-in-part of Ser. No. 605,063, Apr. 30, 1984, abandoned.

[30] Foreign Application Priority Data

Apr. 29, 1983 [LU] Luxembourg .......................... 84784
Dec. 29, 1983 [LU] Luxembourg .......................... 85161

[51] Int. Cl.$^4$ .................. C07K 17/06; C07K 15/14; C07K 15/00
[52] U.S. Cl. ......................... 530/363; 514/21; 530/362; 530/391; 530/405; 530/409
[58] Field of Search ............ 530/409, 405, 391, 363, 530/362

[56] References Cited

U.S. PATENT DOCUMENTS 4,522,750  6/1985  Ades et al. .................. 530/397
4,596,676  6/1986  Cullinan ....................... 530/391 X
4,801,688  1/1989  LaGuzza et al. ............. 530/391

Primary Examiner—Howard E. Schain
Attorney, Agent, or Firm—Ostrolenk, Faber, Gerb & Soffen

[57] ABSTRACT

The invention relates to new conjugates of vinblastine and some of its known derivatives with proteins, fragments thereof, aminoacids or amines, which are useful as anti-tumor agents. The invention also relates to some intermediates which are active in chemotherapy, and amino derivatives thereof.

These compounds correspond to the following general formula

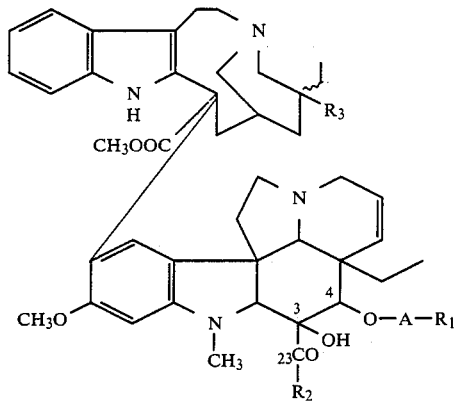

in which
A represents an acetylamino-, trifluoroacetylamino- or carbobenzyloxyamino- substituted —CO(CH$_2$)$_n$CO—

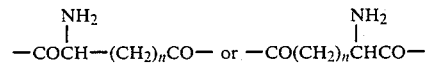

in which n is 1 to 5,
R$_1$ represents an optionally modified protein radical,
R$_2$ represents a methoxy group, an amino group or an alpha-aminoacid ester radical which is bonded via a bond of the amide type and in which the ester group contains 1 to 6 carbon atoms, and R$_3$ represents hydrogen or hydroxyl.

21 Claims, No Drawings

CONJUGATES OF VINBLASTINE, A PROCESS FOR THEIR PREPARATION AND THEIR USE IN THERAPY

This is a continuation-in-part of application Ser. No. 605,063 filed Apr. 30, 1984, now abandoned.

The present invention relates to new conjugates of vinblastine and of some of its known derivatives with i.a. proteins, a method for obtaining them and their use as an anti-tumour agent. The invention also relates to some intermediates which are active in chemotherapy, and to amino derivatives thereof.

Vinblastine and some of its derivatives, in particular vincristine or vindesine, have already been coupled to proteins, for example albumin or various immunoglobulins. Coupling products or compounds called "conjugates" result. The following literature references may be referred to in particular: J. D. Teale, Jacqueline M. Clough and V. Marks, Br. J. Clin. Pharmac. 4, 169–172, 1977; C. H. J. Ford, C. E. Newman, J. R. Johnson, C. S. Woodhouse, T. A. Reeder, G. F. Rowland, R. G. Simmonds, Br. J. Cancer 47, 35–42, 1983; M. J. Embleton, G. F. Rowland, R. G. Simmonds, E. Jacobs, C. H. Marsden, R. W. Baldwin, Br. J. Cancer 47, 43–49, 1983; J. R. Johnson, C. H. J. Ford, C. E. Newman, C. S. Woodhouse, G. F. Rowland, R. G. Simmonds, Br. J. Cancer 44, 472–475, 1982; Eli Lilly Eur. Pat. Applic., Publ. No. 56.322, 21.07.82; and R. A. Conrad, G. J. Cullinan, K. Gerzon, G. A. Poore, J. Med. Chem. 22, 391, 1979.

Coupling of these bis-indole derivatives has been effected not only with the aim of developing new immunological reagents, but in particular with the aim of preparing anti-tumour substances which are more active, more selective and less toxic.

In this last respect, numerous conjugates of proteins with other anti-tumour agents are currently being studied. This applies, in particular, to conjugates of antibodies and a fragment of ricin or conjugates of albumin and methotrexate (French Patent Application No. 2,437,213, C M Industries; and B. C. F. Chu, S. B. Howell, J. of Pharmacology and Exp. Therapeutics, 219 (2), 389–393, 1981).

Monoclonal antibodies, in particular those of human origin, coupled to known anti-tumour medicaments are more particularly the subject of various studies.

Finally, reference is made to the fact that the use and evaluation of 1:1 complexes of bis-indole alkaloids with tubulin have been described in Belgian Pat. No. 854,053. In some cases, a lower toxicity and a more significant chemotherapeutic activity than from the corresponding free alkaloids may result.

The present invention is particularly directed to conjugates of vinblastine or of derivatives of vinblastine with proteins, fragments of proteins, aminoacids or simple amines, characterised in that the coupling is effected by means of an ester group derived from the hydroxyl group of the carbon 4 of the vinblastine skeleton. The derivatives of 4-O-deacetylvinblastine may be, for example, vindesine, 4-O-deacetylvinblastine or 4-O-deacetyl-deoxy-4'-vinblastine coupled at C-3 with an ester of an aminoacid.

More particularly, the compounds according to the invention correspond to the following general formula:

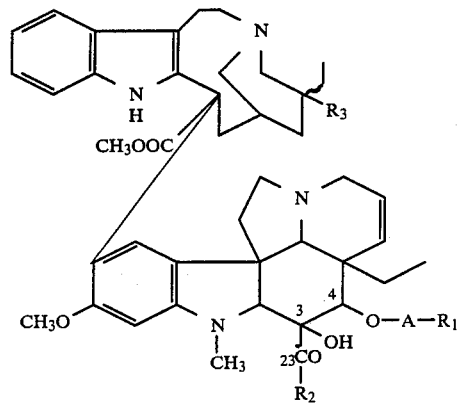

in which A represents acetylamino-, trifluoroacetylamino- or carbobenzyloxyamino-substituted $-CO(CH_2)_n-CO-$, or

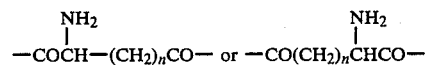

in which n varies from 1 to 5, $R_1$ represents an optionally modified protein radical, $R_2$ represents a methoxy group, an amino group or an alpha-aminoacid ester radical which is bonded by a bond of the amide type and in which the ester group contains 1 to 6 carbon atoms, and $R_3$ represents a hydrogen atom or a hydroxyl group, in each case in the two possible configurations, and its addition salts with an inorganic or organic acid.

It goes without saying that the arm of the acetate, hemisuccinate or hemiglutarate type or of the type of a higher homologue can be substituted, for example by an alkyl or an amino group or a protected amino group, whilst preserving the activity which characterises the compounds according to the invention.

In the prior art, bonding was effected by means of an amide bond at the 23-vinblastinoyl function of the bisindole derivative. Surprisingly, we have found that the anti-tumour activity can be better preserved if bonding is effected at C-4 rather than C-23.

The derivatives according to the present invention are obtained, in a first stage, by condensation of chloroacetyl chloride or an anhydride, for example chloroacetic anhydride, succinic anhydride, glutaric anhydride or a higher homologue, onto the hydroxyl at C-4 of 4-O-deacetylvinblastine or one of the derivatives of the 4-O-deacetylvinblastine-3-carboxamide type.

The 4-chloroacetate, 4-hemisuccinate or 4-hemiglutarate derivatives thus obtained are then condensed with the protein, the aminoacid or the simple amine in a solvent in which these compounds are soluble. For this purpose, a water/dioxane mixture at a suitable pH maintained by a buffer, for example a borate buffer, can be used. The condensation is confirmed by chromatography or electrophoresis. In the latter case, radioactive (for example tritiated) vinblastine may be used in order to facilitate the characterisation.

The preparation of the chloroacetate at C-4 of vinblastine is described by W. W. Hargrove Lloydia, 27 (4), 342, 1964. It can accordingly be obtained by the action of chloroacetic anhydride on deacetyl-vinblastine in methylene chloride.

From the chemical point of view, the condensation with the proteins can be explained by the production of covalent bonds resulting from the reaction of the amine groups of the protein lysine with the activated chlorine of the chloroacetate function or with the activated ester group derived from the hemisuccinate or hemiglutarate.

Bovine serum albumin, for example, contains 56 amine residues of lysine. The number of molecules of vinblastine per protein varies as a function of the operating conditions, but is generally between 1 and 34.

The activation can be effected in a conventional manner by treatment with an alkyl chloroformate, preferably ethyl or isobutyl chloroformate, in the presence of an amine base, such as N-methylpiperidine or N-methylmorpholine.

The condensation can be carried out in situ on the reaction mixture containing the activated anhydride. However, in most cases, the activated anhydride can also be isolated.

The conjugate obtained is isolated by means of the conventional methods used in chemistry or, in the case of protein conjugates, in biochemistry. The protein conjugate is accordingly precipitated out of the reaction mixture by addition of acetone and is centrifuged off, rinsed, lyophilised and purified by gel filtration. If appropriate, the derivative thus obtained may be subjected to a conventional succinylation reaction, which enables the aggregation problems which characterise certain conjugated and non-conjugated proteins to be avoided.

The proteins which can advantageously be used are, in particular, bovine or human serum albumin, fetuin or immunoglobulins, the latter being obtained, if appropriate, by the monoclonal antibody technique. In the latter case, the use of monoclonal antibodies of human origin which demonstrate a certain specificity towards human tumours has proved to be of particular interest.

The proteins used can also be treated in order to be selectively modified. These modifications enable protein conjugates to be obtained which, during use in therapy, are concentrated preferentially in certain tissues, for example in the liver. It is thus possible, prior to the condensation of the derivative of the vinblastine with the protein, to galactosylate the latter. The galactosylation is carried out, for example, by applying the method described by G. Wilson in The Journal of Biochemistry, 253 (7) 2070-2072, 1978.

In vitro experiments carried out with the compounds according to the invention to demonstrate their antitumour activity indicate that the formation of the conjugate by a bond at C-4 may be more advantageous than if the bond is effected at C-3.

Coupling via the carbon 3 of vinblastine or its derivatives is carried out in a conventional manner by forming, in a first stage, the hydrazide at C-23 (carbohydrazide) and forming the hydrazoate of the corresponding acid by nitrosation. The hydrazoate is thus coupled directly to the protein.

However, this acid hydrazoate can also be condensed, in a manner which is likewise known, with an aminoacid ester, for example a methyl ester. The ester function of the aminoacid can in turn be subjected to hydrazinolysis and nitrosation. The new acid hydrazoate of the aminoacid-vinblastine coupling product is then condensed with the protein. The aminoacid in this case constitutes the bond uniting the protein to the vinblastine molecule.

Examples of condensation derivatives coupled at C-4 and 4-O-deacetylated thus obtained are those of the following types:

coupling via the carbon C-4: vindesine-O-4-chloroacetate (Example 1), vindesine-O-4-chloroacetate+bovine serum albumin (BSA-VDS-C-4) (Example 2), vindesine-O-4-chloroacetate+succinylated bovine serum albumin (BSA(S)-VDS-C-4) (Example 2), vindesine-O-4-chloroacetate+human serum albumin (HA-VDS-C-4) (Example 3a), vindesine-O-4-chloroacetate+galactosylated human serum albumin (HAgal-VDS-C-4) (Example 3b), vindesine-O-4-chloroacetate+pyrrolidine, ethyl vinblastine-C-3-isoleucinate-O-4-chloroacetate (Example 4), ethyl vinblastinoyl-23-isoleucinate-O-4-chloroacetate+succinylated bovine serum albumin (BSA(S)-VIIe-C-4) (Example 4), vindesine-O-4-hemisuccinate+pyrrolidine (Example 5), vindesine-O-4-hemisuccinate+bovine serum albumin (BSA-Succ-VDS) (Example 6), vindesine-O-4-hemisuccinate+human serum albumin (HA-Succ-VDS) (Example 7), vindesine-O-4-hemisuccinate+galactosylated human serum albumin (HAgal-Succ-VDS) (Example 8), vindesine-O-4-hemisuccinate+non-specific immunoglobulins (IgG)(IgG-Succ-VDS) (Example 9), vindesine-O-4-hemisuccinate+IgG anti-milk fat globule (IgG-anti MFG) (IgG anti-MFG-Succ-VDS) (Example 10), vinblastine-O-4-hemisuccinate+pyrrolidine (Example 11), vinblastine-O-4-hemisuccinate+ethyl tryptophanate (Example 12), ethyl deoxyvinblastinoyl-23-tryptophanate-O-4-hemisuccinate+pyrrolidine (Example 14), ethyl deoxyvinblastinoyl-23-tryptophanate-O-4-hemisuccinate+bovine serum albumin (BSA-Succ-DeoxyvTrpE) (Example 14), deoxyvindesine-O-4-hemisuccinate+ethyl tryptophanate (Example 15), ethyl vinblastinoyl-23-tryptophanate-O-4-hemisuccinate+pyrrolidine (Example 16) and vinblastine-O-4-hemiglutarate+pyrrolidine (Example 17).

The following examples illustrate, non-limitatively, the process which gives the compounds according to the invention.

EXAMPLE 1

Vindesine-O-4-chloroacetate 0.92 mmol of vindesine, 25 ml of $CH_2Cl_2$ and 4.1 mmol of chloroacetic anhydride are introduced into a flask. The solution is stirred in the absence of light for 14 hours. 25 ml of methanol are added. The mixture is stirred at room temperature for 2 hours. The solvent is evaporated off in vacuo, the residue is dissolved in 500 ml of $CH_2Cl_2$ and the solution is washed with a cold dilute aqueous solution of $NH_4OH$. After evaporation of the organic phase, the residue is dissolved in 47 ml of methanol containing 11.2 ml of water and 2.33 g of silica. The mixture is stirred at room temperature for 6 hours. The silica is separated off by filtration and washed several times with hot methanol. The filtrate is concentrated in vacuo, rendered alkaline with a dilute solution of ammonia and extracted with $CH_2Cl_2$. The extracts are combined, dried over $Na_2SO_4$ and evaporated to dryness. Purification is carried out over a silica column by eluting with a mixture of $CH_2Cl_2$:5% MeOH. Yield: 88%.

IR: 3470, 3040, 2970, 2880, 1740, 1690, 1615, 1510, 1500, 1430, 1225, 1190, 1010 and 740 $cm^{-1}$.

Mass spectrum: 830 (M+1), 813, 796, 773, 754, 297, 277, 293 and 108.

Nucleomagnetic resonance spectrum: ppm 8 (1H, s, NHind), 7.45 (1H, d), 7.2–7.0 (4H, m), 6.9 (1H, d), 6.5 (1H, s), 6.05 (1H, s), 5.8 (1H, m), 5.5 (1H, m), 5.28 (1H, d), 4.0 (2H, CH$_2$Cl), 3.7 (3H, s, —CO$_2$CH$_3$), 3.55 (3H, s, OCH$_3$), 2.8 (3H, s, NCH$_3$) and 0.9–0.65 (8H, m).

EXAMPLE 2

(a) Coupling at the C-4 of O-4-deacetyl-vindesine (BSA-VDS-C-4)

The chloroacetate at C-4 of radioactive O-4-deacetyl-vindesine (150 mg), dissolved in 5 ml of dioxane, is added dropwise to a solution of 216 mg of BSA (bovine serum albumin, Cal Biochem) in 5 ml of 0.4M borate buffer of pH 9.0. The mixture is stirred at room temperature for 48 hours. The conjugate is precipitated by addition of 6 volumes of acetone and centrifuged for 30 minutes at 1,300 rpm. The precipitate is washed twice with acetone and centrifuged under the same conditions. After these two rinsings, the precipitate is lyophilised and purified by filtration over G-25 gel (3×90 cm) equilibrated in a solution of 0.1M NH$_4$HCO$_3$ of pH 7.8. The excluded peak is recovered and lyophilised. The protein content is measured by the Lowry technique and the alkaloid content is estimated by measurement of the radioactivity. The conjugate obtained contains 2.5 mol of vindesine per mol of BSA. Chromatography on agarose gel demonstrates that the radioactivity is firmly united with the proteins.

(b) Succinylation (BSA(S)-VDS-C-4)

The conjugate is dissolved in water in a concentration of 100 mg/5 ml of water and the pH of the solution is brought to 7 with a 0.1N solution of NaOH. 55 mg of succinic anhydride are then added in small fractions. The pH is kept at 7 by addition of 0.1N NaOH. When the pH has stabilised, a further 55 mg of succinic anhydride are added. The solution is stirred at room temperature for 1 hour, dialysed against water at 0° C. overnight and lyophilised. The protein and alkaloid contents are estimated according to the techniques described in (a).

EXAMPLE 3

(a) Coupling of C-4 of O-4-deacetyl-vindesine (HA-VDS-C-4)

The chloroacetate at C-4 radioactive O-4-deacetyl-vindesine (140 mg), dissolved in 3 ml of dioxane, is added dropwise to a solution of 200 mg of human albumin (Mérieux) in 2 ml of 0.34M borate buffer of pH 9.0. The mixture is stirred at room temperature for 24 hours. The conjugate is precipitated by addition of 6 volumes of acetone and the mixture is centrifuged for 30 minutes at 1,300 rpm. The precipitate is washed twice with acetone and centrifuged under the same conditions. After these two rinsings, the precipitate is lyophilised and purified by filtration over G-25 gel (3×90 cm), equilibrated in a solution of 0.1M NH$_4$HCO$_3$ of pH 7.8. The excluded peak is recovered and lyophilised. The protein content is measured by the Lowry technique and the alkaloid content is estimated by measurement of the radioactivity. The conjugate obtained contains 2.6 mol of vindesine per mol of HA.

(b) Coupling of C-4 of O-4-deacetyl-vindesine (HAgal-VDS-C-4)

The chloroacetate at C-4 of radioactive 4-O-deacetyl-vindesine (51 mg), dissolved in 2 ml of dioxane, is added dropwise to a solution of 200 mg of HAgal in 17 ml of PBS (phosphate-buffered saline) and 3.4 ml of 1.7N borate of pH 9. The mixture is stirred at room temperature for 24 hours. The conjugate is precipitated by addition of 6 volumes of acetone and the mixture is centrifuged for 30 minutes at 1,300 rpm.

The precipitate is washed twice in acetone and centrifuged under the same conditions. After these two rinsings, the precipitate is lyophilised and purified by filtration over G-25 gel (3×90 cm), equilibrated in a solution of 0.1M NH$_4$HCO$_3$ of pH 7.8. The excluded peak is recovered and lyophilised. The protein content is measured by the Lowry technique and the alkaloid content is estimated by measurement of the radioactivity. The conjugate obtained contains 0.4 mol of vindesine per mol of HAgal.

EXAMPLE 3

4-O-Chloroacetate of ethyl N-(4-O-deacetyl-3-decarbomethoxy-vinblastin-23-oyl)-L-isoleucinate (BSA(S)-VIIa-C-4)

By the procedure of Example 1, starting from the corresponding derivative of vinblastine (see Belgian Pat. No. 889,136), the ethyl vinblastine-C-3-isoleucinate-O-4-chloroacetate derivative is obtained with a yield of 85%.

Infra-red spectrum: 3470, 3410, 3040, 2970, 2880, 1740, 1680, 1615, 1460, 1430, 1300, 1225, 1190, 1150, 1010 and 740 cm$^{-1}$.

Mass spectrum: 988 (M+17), 973 (M+2), 939, 917, 391, 236 and 94.

Nucleomagnetic resonance spectrum: ppm 9.85 (1H, s, OH), 8.6 (1H, s, NH), 7.55 (1H, d), 7.4 (1H, d), 7.2–7.0 (m, 3H), 6.65 (1H, s), 6.1 (1H, s), 5.85 (1H, m), 5.58 (1H, s), 5.32 (1H, m), 4.6 (1H, q), 4.2 (2H, m), 4.0 (2H), 3.78 (3H, s), 3.1 (3H, s), 2.7 (3H, s), 1.28 (3H, t) and 1.0–0.8 (14H, m).

By the procedure described in Example 3, BSA(S)-VIIe-C-4 is obtained.

EXAMPLE 5

Vindesine-4-O-hemisuccinate-pyrrolidinamide

Starting from vindesine and following a procedure analogous to that in Example 11, the corresponding conjugate is obtained with a yield of 62%.

Mass spectrum (DCI, isobutane): 921 (M+14) and 907 (M)

IR (CHCl$_3$, 4%): 3400, 2975, 2882, 1732, 1693, 1632, 1503, 1462, 1380 and 1247 cm$^{-1}$.

NMR (360 MHz, CDCl$_3$): 8.05 (1H, H17), 5.46 (1H, H15), 3.96 (1H, H17'a), 3.80 (3H, OMe); 3.64 (3H, OMe), 3.45 (2CH$_2$-pyrrolidine), 2.88 (3H, N—CH$_3$), 0.95 (3H, CH$_3$) and 0.83 (3H, CH$_3$).

EXAMPLE 6

Formation of the hemisuccinate at 4-O of vindesine and coupling with bovine serum albumin (BSA) (BSA-Succ-VDS)

0.125 mmol of vindesine, 0.187 mmol of succinic anhydride and 4 ml of anhydrous CH$_2$Cl$_2$ are introduced into a flask. The solution is stirred, while shielded from light, at room temperature for 14 hours. The solution is then immersed in an ice-bath. 0.250 mmol of triethylamine, 0.250 mmol of ethyl chloroformate and 5 ml of dioxane are added. The mixture is stirred for ½ hour. In a separate operation, a solution of 90 mg of BSA in 17.3 ml of H$_2$O is prepared, and 17.3 ml of dioxane are added dropwise. The pH is adjusted to 8.5 with 1N sodium hydroxide solution. The solution is cooled to 5° C. After ½ hour, the activated ester is added to the solution of BSA. The solution is stirred at 5° C. for 4 hours, during which the pH is kept at 8.5 by addition of 1N NaOH. Precipitation of the conjugate and its characterisation are carried out as described above. The molar ratio is about 18:1 and remains constant after chromatography on Sepharose 6B in the presence of 6M guanidine.

EXAMPLE 7

Vindesine-4-O-hemisuccinate and coupling with human albumin (HA) (HA-Succ-VDS)

0.28 mmol (210 mg) of vindesine, 42 mg (0.4 mmol) of succinic anhydride and 6 ml of anhydrous $CH_2Cl_2$ are introduced into a flask. The solution is stirred, while shielded from light, at room temperature for 14 hours. The solvent is evaporated. The residue is taken up in 4.7 ml of dioxane. The solution is then immersed in an ice-bath. 0.56 mmol of triethylamine in 3.5 ml of dioxane and 0.56 mmol of isobutyl chloroformate in 3.5 ml of dioxane are added.

The mixture is stirred for 1 hour. In a separate operation, a solution of 208 mg of HA in 38 ml of $H_2O$ is prepared, and 26 ml of dioxane are added dropwise. The pH is adjusted to 8.5 with 1N sodium hydroxide solution. The solution is cooled to 5° C. After 1 hour, the activated ester is added to the solution of human albumin. The solution is stirred at 5° C. for 14 hours, during which the pH is kept at 8.5 by addition of 1N NaOH. Precipitation of the conjugate and its purification are carried out as described above. The molar ratio is 13.8:1.

EXAMPLE 8

Vindesine-4-O-hemisuccinate and coupling with galactosylated human albumin (HAgal) (HAgal-Succ-VDS)

0.16 mmol (119 mg) of vindesine, 0.24 mm (25 mg) of succinic anhydride and 3.4 ml of anhydrous $CH_2Cl_2$ are introduced into a flask. The solution is stirred, while shielded from light, at room temperature for 14 hours. The solvent is evaporated. The residue is taken up in 2.7 ml of dioxane. The solution is then immersed in an ice-bath. 0.32 mmol of triethylamine in 2 ml of dioxane and 0.32 mmol of isobutyl chloroformate in 2 ml of dioxane are added. The mixture is stirred for 1 hour.

In a separate operation, a solution of 164 mg of HAgal in 17.5 ml of $H_2O$ is prepared, and 25 ml of dioxane are added dropwise. The pH is adjusted to 8.5 with 1N sodium hydroxide solution. The solution is cooled to 5° C. After 1 hour, the activated ester is added to the solution of HAgal. The solution is stirred at 5° C. for 14 hours, during which the pH is kept at 8.5 with 1N sodium hydroxide solution. Precipitation of the conjugate with its purification are carried out as described above. The molar ratio is 21.6:1.

EXAMPLE 9

Vindesine-4-O-hemisuccinate and coupling with non-specific immunoglobulins from goat serum (IgG) (IgG-Succ-VDS)

0.07 mmol (50 mg) of vindesine, 0.1 mmol of succinic anhydride and 4 ml of anhydrous $CH_2Cl_2$ are introduced into a flask. The solution is stirred, while shielded from light, at room temperature for 14 hours. The solvent is evaporated. The residue is taken up in 1 ml of dioxane. The solution is then immersed in an ice-bath. 0.14 mmol of triethylamine and 0.14 mmol of isobutyl chloroformate are added. The mixture is stirred for 1 hour. In a separate operation, a solution of 66 mg of IgG in 12.7 ml of $H_2O$ is prepared, and 12.7 ml of dioxane are added dropwise. The pH is adjusted to 8.5 with 1N sodium hydroxide solution. The solution is cooled to 5° C. After 1 hour, the activated ester is added to the solution of IgG. The solution is stirred at 5° C. for 14 hours, during which the pH is kept at 8.5 by addition of 1N NaOH. Precipitation of the conjugate and its purification are carried out as described above. The molar ratio is 9:1.

EXAMPLE 10

Vindesine-4-O-hemisuccinate and coupling with polyclonal anti-milk fat globule immunoglobulins (IgG-anti-MFG) (IgG-anti-MFG-Succ-VDS)

0.035 mmol of VDS (25 mg), 0.05 mmol of succinic anhydride and 1 ml of anhydrous $CH_2Cl_2$ are introduced into a flask. The solution is stirred, while shielded from light, at room temperature for 14 hours. The solvent is evaporated and the residue is taken up in 0.25 ml of dioxane. The solution is then immersed in an ice-bath. 0.07 mmol of triethylamine and 0.07 mmol of isobutyl chloroformate are added. The mixture is stirred for 1 hour. In a separate operation, a solution of 25 mg of IgG-anti-MFG in 21.3 ml of $H_2O$ is prepared. The pH is adjusted to 10.5 with 1N sodium hydroxide solution. The solution is cooled to 5° C. After 1 hour, the activated ester is added to the solution of IgG-anti-MFG. The solution is stirred at 5° C. for 14 hours, during which the pH is kept at 8.5 by addition of 1N NaOH. The conjugate is dialysed against 9% strength NaCl and purified on Sephadex G25 as described above. The molar ratio is 15:1.

EXAMPLE 11

Vinblastine-4-O-hemisuccinate-pyrrolidinamide (DAVLB-pyrrolidino)

97.6 mg (0.976 mmol) of succinic anhydride are added to a solution of 500 mg (0.651 mmol) of 4-O-deacetylvinblastine in 15 ml of anhydrous methylene chloride. The solution is stirred at room temperature for 20 hours. It is then cooled to 0° C. with an ice-bath and a solution of 131.5 mg (1.303 mmol) of triethylamine in 8 ml of methylene chloride and a solution of 141.2 mg (1.302 mmol) of ethyl chloroformate in 8 ml of methylene chloride are added successively. The mixture is stirred at 0° C. for 1 hour 30 minutes and 92.5 mg (1.302 mmol) of pyrrolidine dissolved in 8 ml of methylene chloride are added. The mixture is allowed to return to room temperature and is stirred for 2 hours. 50 ml of methylene chloride and 50 ml of a 10% strength aqueous solution of sodium carbonate are added. The mixture is stirred, and allowed to settle and the organic phase is separated off. The organic phase is extracted 3 times with methylene chloride. The combined organic phases are washed with a saturated aqueous solution of NaCl and dried over $MgSO_4$.

The residue obtained after evaporation is purified by chromatography over a column of $SiO_2$ (elution: methylene chloride/methanol 92:8). After trituration in a mixture of ethyl acetate/cyclohexane, 386 mg of pure product are thus obtained in the form of an amorphous powder. Yield: 64%.

Mass spectrum: DCl (isobutane): 936 (M+14) and 922 (M)

IR (CHCl$_3$, 5%): 3477, 3015, 2980, 2885, 1741, 1635, 1505, 1450 and 1250 cm$^{-1}$ Nucleomagnetic resonance spectrum: (CDCl$_3$, 360 MHz, ppm): 8.05 (NH, 1H), 7.53 (1H), 7.16 (3H), 6.66 (1H), 6.10 (1H), 5.85 (1H) and 5.45 (1H) (H14, H15), 5.51 (1H, H17), 3.95 (1H, H17'a), 3.78 (3H, OMe), 3.75 (3H, OMe), 3.60 (3H, OMe), 3.70 (1H, H2), 3.43 (7H), 3.11 (2H, H5'b+H6'b), 2.78 (2H, H21a'+H21'b), 2.70 (3H, NMe), 2.61 (1H, H21), 2.25 (1H, H17'), 1.90 (2H, CH$_2$-CO), 1.80 (2H, CH$_2$CO), 1.73 (2H, beta-pyrrolidine), 1.28 (2H, idem.), 1.45 (1H, H15'a), 1.37 (1H, H14'b), 0.86 (3H, CH$_3$), 0.80 (3H, CH$_3$) and 0.76 (1H, H14').

EXAMPLE 12

Vinblastine-4-O-hemisuccinate+ethyl tryptophanate 52 mg (0.524 mmol) of succinic anhydride are added to a solution of 0.310 g (0.403 mmol) of 4-O-deacetyl-vinblastine in 7 ml of anhydrous methylene chloride. The solution is stirred at room temperature for 15 hours and cooled to 0° C. After successive addition of a solution of 81 mg (0.806 mmol) of triethylamine in 5 ml of methylene chloride and of a solution of 87 mg of ethyl chloroformate in 5 ml of methylene chloride, the reaction mixture is stirred at 0° C. for 1 hour 30 minutes. 187 mg (0.806 mmol) of ethyl L-tryptophanate, dissolved in 7 ml of methylene chloride, are then added. The mixture is allowed to return to room temperature and is stirred for 15 hours.

The solution is then treated as in Example 12. The residue obtained is purified by chromatography over a column of SiO$_2$ (elution: ether/methanol saturated with NH$_3$, 92:8). 305 mg of pure product are thus obtained in the form of a white powder, after trituration in isopropanol. Yield: 70%.

Mass spectrum (DCl, isobutane): 1097 (M+14) and 1083 (M)

IR (CHCl$_3$): 3460, 2995, 2960, 2870, 1735, 1669, 1613, 1502, 1457, 1331, 1251, 1167 and 1010 cm$^{-1}$ UV (methanol, maximum, log): 216 (4.87), 265 (4.27) and 288 (3.01)

NMR (360 MHz, CDCl$_3$): 8.44 (1H, NH), 8.08 (1H, NH), 7.52 (2H), 7.33 (1H), 7.10 (6H), 6.66 (1H, H9), 6.06 (1H, H12), 5.86 (1H, H14), 5.50 (1H, H17), 5.38 (1H, H15), 4.91 (1H), 4.10 (2H, CH$_2$-O), 3.76 (3H, OMe), 3.72 (3H, OMe), 3.63 (3H, OMe), 3.13 (2H, H5'b+H6'b), 2.80 (H21'), 2.68 (NCH$_3$), 0.90 (CH$_3$, 3H), 0.78 (CH$_3$, 3H) and 0.74 (H14').

EXAMPLE 13

Coupling of ethyl N-(4-O-deacetyl-4-O-hemisuccinate-deoxy-vinblastin-23-oyl)-tryptophanate with pyrrolidine A solution of 400 mg (0.419 mmol) of ethyl N-(4-O-deacetyl-deoxy-vinblastin-23-oyl)-tryptophanate (see Belgian Patent 889,136) and 105 mg (1.05 mmol) of succinic anhydride in 20 ml of a mixture of dioxane/toluene (50:50) is refluxed for 3 hours. After distillation of the solvents in vacuo, the residue is dissolved in 20 mmol of anhydrous methylene chloride. After cooling to 0° C. and successive addition of a solution of triethylamine (126 mg, 1.25 mmol) in 5 ml of methylene chloride and of a solution of ethyl chloroformate (136 mg, 1.25 mmol) in 5 ml of methylene chloride, the mixture is stirred for 1 hour. A solution of pyrrolidine (178 mg, 2.5 mmol) in 5 ml of methylene chloride is then added at 0° C. After the solution has returned to room temperature, it is stirred for 4 hours and is then partitioned between 50 ml of methylene chloride and 50 ml of a 5% strength aqueous solution of potassium carbonate. The phases are separated and the aqueous phase is extracted with 2 portions of 20 ml of methylene chloride. The organic extracts are combined, washed successively with 40 ml of water and 40 ml of a saturated aqueous solution of NaCl, dried over magnesium sulphate and evaporated under reduced pressure. The residue is purified by chromatography over SiO$_2$ (elution with CH$_2$Cl$_2$:CH$_3$OH 95:5) and trituration in ether. Yield: 346 mg (75%) of the required compound.

Nucleomagnetic resonance spectrum (CDCl$_3$, 360 MHz) bs=broad singlet: 9.23 (1H, bs, NH), 7.95 (H, bs), 7.45–7.65 (3H, m), 7.33 (1H, m), 7.03–7.21 (6H, m), 6.46 (1H, s), 6.05 (1H, s), 5.83 (1H, m), 5.53 (1H, s), 5.33 (1H, m), 5.01 (1H, m), 4.11 (2H, m), 3.76 (3H, s), 3.58 (3H, s), 3.48 (4H, m), 2.75 (3H, s), 2.65 (1H, s), 2.30 (1H, m), 1.93 (2H, m), 1.85 (2H, m), 1.21 (3H, t), 0.88 (3H, t) and 0.76 (3H, t)

Infra-red spectrum (CHCl$_3$, 5% v:v): 3470, 3003, 2973, 2881, 1732, 1679, 1617, 1501, 1460 and 1180 cm$^{-1}$.

EXAMPLE 14

Ethyl deoxyvinblastin-23-oyl-tryptophanate-4-O-hemisuccinate and coupling with bovine serum albumin (BSA) (BSA-Succ-Deoxy-V-TrpE)

400 mg (0.419 mmol) of deoxy-V-TrpE, 126 mg (1.25 mmol) of succinic anhydride and 20 ml of toluene:dioxane 1:1 are introduced into a flask. The solution is refluxed for 3 hours. The solvents are evaporated and the residue is taken up in 20 ml of dioxane. The solution is then immersed in an ice-bath. 1.26 mmol (126 mg) of triethylamine, 1.25 mmol of isobutyl chloroformate and 5 ml of dioxane are added. The mixture is stirred for 1 hour.

In a separate operation, a solution of 340 mg of BSA in 65 ml of H$_2$O is prepared, and 28 ml of dioxane are added dropwise. The pH is brought to 8.5 with 1N sodium hydroxide solution. The solution is cooled to 5° C. After 1 hour, the activated ester is added to the solution of BSA. The solution is stirred at 5° C. for 14 hours, during which the pH is kept at 8.5 by addition of 1N NaOH. Precipitation of the conjugate and its purification are carried out as described above.

EXAMPLE 15

Coupling of 4-O-deacetyl-4-O-hemisuccinate-deoxy-vindesine with ethyl tryptophanate Following the procedure described in Example 12, but replacing the pyrrolidine with an equimolar amount of ethyl L-tryptophanate, 47% of the required compound is obtained.

Nucleomagnetic resonance spectrum (CDCl$_3$, 360 MHz): 8.45 (1H, bs), 8.02 (1H, bs), 7.50 (2H, m), 7.32 (1H, m), 7.23–7.06 (6H, m), 7.02 (1H, m), 6.50 (1H, s), 6.10 (1H, s), 5.86 (1H, m), 5.50 (1H, s), 5.45 (1H, m), 5.35 (1H, s), 2.86 (3H, s), 2.67 (1H, s), 2.46 (4H, m), 1.30 (3H, t), 0.90 (3H, t) and 0.75 (3H, t).

Infra-red spectrum (CHCl$_3$, 5% v:v): 3480, 3400, 3010, 2978, 2882, 1732, 1690, 1615, 1505, 1460 and 1298 cm$^{-1}$.

EXAMPLE 16

Coupling of ethyl N-(4-O-deacetyl-4-O-hemisuccinatevinblastin-23-oyl)-tryptophanate with pyrrolidine Following the procedure described in Example 13, starting from 700 mg of ethyl N-(4-O-deacetyl-vinblastin-23-oyl)-tryptophanate, 518 mg (64%) of the desired compound are obtained after purification by chromatography over $SiO_2$ and trituration in ethanol.

Nucleomagnetic resonance spectrum ($CDCl_3$, 360 MHz): 8.04 (1H, bs), 7.46–7.63 (3H, m), 7.33 (1H, m), 7.20–7.03 (6H, m), 6.63 (1H, s), 6.08 (1H, s), 5.83 (1H, m), 5.55 (1H, s), 5.33 (1H, m), 5.06 (1H, m), 4.13 (2H, m), 3.96 (1H, m), 3.76 (3H, s), 3.61 (3H, s), 3.46 (4H, m), 3.40 (2H), 2.81 (2H, m), 2.73 (3H, s), 2.65 (1H, s), 1.85 (m), 1.20 (t, 3H), 0.89 (t, 3H) and 0.71 (t, 3H).

Infra-red spectrum ($CHCl_3$ 5%, v:v): 3474, 3002, 2977, 2882, 1730, 1678, 1617, 1500, 1460 and 1173 $cm^{-1}$.

EXAMPLE 17

Coupling of 4-O-deacetyl-4-O-hemiglutarate-vinblastine with pyrrolidine

A solution of 4-O-deacetylvinblastine (700 mg, 0.911 mmol) and glutaric anhydride (145 mg, 1.27 mmol) in 25 ml of anhydrous methylene chloride is stirred, while shielded from light, for 70 hours. After cooling to 0° C. and successive addition of a solution of N-methylpiperidine (163 mg, 1.64 mmol) in 7 ml of methylene chloride and a solution of isobutyl chloroformate (223 mg, 1.64 mmol) in 7 ml of methylene chloride, the mixture is stirred for 1 hour. A solution of pyrrolidine (194 mg, 2.73 mmol) in 7 ml of methylene chloride is then added at 0° C.

After the solution has returned to room temperature, it is stirred for 5 hours. It is then partitioned between 60 ml of methylene chloride and 60 ml of a 5% strength aqueous solution of potassium carbonate. The phases are separated and the aqueous phase is extracted with 2 portions of 30 ml of methylene chloride. The organic extracts are combined, and washed with water and with a saturated aqueous solution of NaCl, dried over $MgSO_4$ and evaporated under reduced pressure. The residue is purified by chromatography over $SiO_2$ (elution: $CH_2Cl_2:CH_3OH$ 95:5) and trituration in a mixture of ethyl acetate:heptane. Yield: 605 mg (71%) of the required compound.

Nucleomagnetic resonance spectrum ($CDCl_3$, 360 MHz): 7.95 (1H, bs), 7.45 (1H, m), 7.16–7.00 (3H, m), 6.55 (1H, s), 6.02 (1H, s), 5.76 (1H, m), 5.40 (1H, s), 5.20 (1H, m), 3.88 (1H, m), 3.71 (6H, 2s), 3.53 (3H, s), 3.38 (4H, m), 2.62 (3H, s), 2.58 (1H, s), 1.92 (4H, m), 1.80 (2H, m), 0.80 (3H, t) and 0.73 (3H, t).

Infra-red spectrum ($CHCl_3$, 5% v:v): 3473, 3003, 2977, 2884, 1738, 1620, 1500, 1460 and 1301 $cm^{-1}$.

The compounds according to the invention have been tested on $BDF_1$ or $DBA_2$ mice into which P388 leukaemia has been introduced interperitoneally or intravenously, the anti-tumour activity being measured by the percentage ILS (Increased Life Span, increase in the survival time).

The experiments carried out with vindesine, ethyl N-(4-O-deacetyl-3-de(methoxycarbonyl)-vinblastin-32-oyl)-tryptophanate (see European Patent Application Publication No. 41,935, Omnichem) and other aminoacid derivatives at C-4, coupled via the carbon C-3 with fetuin or bovine serum albumin in a ratio of from 2:1 to 6:1, thus demonstrate that these conjugates have little activity on P388 tumors (see table).

The conjugate was administered intraperitoneally or intravenously, in an identical manner to the injection of the tumour.

In contrast, the same substances on which coupling is effected at C-4 show, surprisingly, a significant activity when used in similar tests. Increases in the survival time of more than 70% were observed.

The superior activity of the protein conjugates according to the present invention has also been demonstrated on L1210 cells in vitro in RPMI medium containing 10% foetal calf serum. After incubation, the technique adopted consists in measuring the cell protein content, the calculation being carried out by adopting the Lowry technique. Thus, after 3 days at a concentration of 10–50 microgrammes/ml of BSA(S)-C4-VDS, an inhibition in cell growth is obtained, whilst the untreated cell culture has multiplied by a factor of 2.5.

Hep. G2 hepatoma cells (300,000 cells) were incubated for 8 days in the presence of HAgal-VDS-C-4 and HAgal-VDS-C-3 at concentrations ranging from 1.3 to 21,700 ng of VDS/ml. After 8 days, the cell protein is estimated by the Lowry technique. The results show that the drug concentration which kills 50% of the cells is greater than 1,000 ng/ml in the case of HAgal-VDS-$C_3$ and is 215 ng/ml in the case of HAgal-VDS-$C_4$.

TABLE

ACTIVITIES OF DERIVATIVES OF VINBLASTINE AGAINST TUMOURS INDUCED IN MICE

| PRODUCTS | (a) | (b) | (c) | (d) | (e) | (f) | (g) | (h) |
|---|---|---|---|---|---|---|---|---|
| BSA—TrpV—C-3 | 2 | 10 | 423 | $DBA_2$ | $10^4$ | P388 | iv | 9.4 |
| BSA(S)TrpV—C-3 | 2 | 6.3 | 261 | $DBA_2$ | $10^4$ | P388 | iv | −8 |
| Fet—VDS—C-3 | 6 | 15 | 298 | $BDF_1$ | $10^6$ | P388 | ip | 4.1 |
| Fet(S)—VDS—C-3 | 2 | 15 | 298 | $BDF_1$ | $10^6$ | P388 | ip | 8.2 |
| Fet—ILe—VDSC3 | 2 | 10 | 294 | $BDF_1$ | $10^6$ | P388 | ip | 2.6 |
| BSA—VDS—C-4 | 1.7 | 8 | 398 | $BDF_1$ | $10^6$ | P388 | ip | 2 |
|  | 2.7 | 16 | 500 | $BDF_1$ | $10^6$ | P388 | ip | 48 |
| BSA(S)—VDS—C-4 | 2.5 | 10 | 332 | $BDF_1$ | $10^6$ | P388 | ip | 76 |
|  | 2.4 | 27.5 | 968 | $BDF_1$ | $10^6$ | P388 | ip | 71 |
| BSA(S)—VIIe—C-4 | 1.3 | 3 | 165 | $BDF_1$ | $10^6$ | P388 | ip | 18 |
|  | 1.3 | 10 | 550 | $BDF_1$ | $10^6$ | P388 | ip | 20 |
|  | 1.3 | 14 | 771 | $BDF_1$ | $10^6$ | P388 | ip | 32 |
| BSA—Succ—VDS | 18 | 35 | 173 | $BDF_1$ | $10^6$ | P388 | ip | 39 |
|  | 18 | 75 | 371 | $BDF_1$ | $10^6$ | P388 | ip | 79 |
| BSA(S)—Succ—VDS | 32 | 35 | 97 | $BDF_1$ | $10^6$ | P388 | ip | 39 |
| BSA(S)—Succ—VDS | 32 | 75 | 208 | $BDF_1$ | $10^6$ | P388 | ip | 79 |

TABLE-continued
ACTIVITIES OF DERIVATIVES OF VINBLASTINE AGAINST TUMOURS INDUCED IN MICE

| | (a) | (b) | (c) | (d) | (e) | (f) | (g) | (h) |
|---|---|---|---|---|---|---|---|---|
| (passed over guanidine) | 32 | 75 | 208 | BDF$_1$ | $10^6$ | P388 | ip | 58 |
| BSA—Succ—VDS | 34 | 75 | 196 | BDF$_1$ | $10^6$ | P388 | ip | 42 |
| BSA—Succ—VDS | 19 | 75 | 351 | BDF$_1$ | $10^6$ | P388 | ip | 36 |
| (passed over animal charcoal) | 16.6 | 75 | 403 | BDF$_1$ | $10^6$ | P388 | ip | 47 |
| (passed over guanidine) | 17 | 75 | 393 | BDF$_1$ | $10^6$ | P388 | ip | 42 |
| IgG—nonspec-Succ—VDS | 24 | 75 | 643 | BDF$_1$ | $10^6$ | P388 | ip | 77 |
| HAgal—Succ—VDS | 21.6 | 75 | 356 | BDF$_1$ | $10^6$ | P388 | ip | 57 |
| BSA—Succ—deoxy-VTrpE | | | 146 | BDF$_1$ | $10^6$ | P388 | ip | 37 |
| BSA—Succ—deoxy-VTrpE | | | 284 | BDF$_1$ | $10^6$ | P388 | ip | 52 |

| | (b) | (d) | (e) | (f) | (g) | (h) |
|---|---|---|---|---|---|---|
| VDS—chloroacetate | 4 | DBA$_2$ FR | $10^5$ | P388 | iv | |
| | 8 | DBA$_2$ FR- | $10^5$ | P388 | iv | 38 |
| | 10 | DBA$_2$ FR | $10^5$ | P388 | iv | 57 |
| | 14 | DBA$_2$ FR | $10^5$ | P388 | iv | 70 |
| | 12 | DBA$_2$ US | $10^5$ | P388 | iv | 63 |
| | 15 | BDF$_1$ | $10^6$ | P388 | ip | >60 |
| VILE—chloroacetate | 4 | DBA$_2$ | $10^6$ | P388 | ip | 24 |
| | 8 | DBA$_2$ | $10^6$ | P388 | ip | 52 |
| | 12 | DBA$_2$ | $10^6$ | P388 | ip | 80 |
| | 16 | DBA$_2$ | $10^6$ | P388 | ip | −29 |
| DAVLB—pyrrolidino | 6.25 | DBA$_2$ | $10^5$ | P388 | iv | 9 |
| | 12.5 | DBA$_2$ | $10^5$ | P388 | iv | 20 |
| | 25 | DBA$_2$ | $10^5$ | P388 | iv | 43 |
| | 50 | DBA$_2$ | $10^5$ | P388 | iv | 82 |

(a) molar ratio of vinca:protein
(b) dose in mg of vinca/kg
(c) dose in mg of protein/kg
(d) strain of mouse
(e) number of cells injected
(f) type of tumour injected
(g) injection route
(h) percentage increase in the survival time of the survivors in comparison with untreated mice (ILS)

The present invention thus also relates to industrial and, in particular, pharmaceutical uses of the new bisindole compounds.

In fact, the compounds according to the invention have particularly useful anti-tumour properties which are capable of being used in human therapy.

In particular, these vinblastine derivatives can be used for the treatment of leukaemias, gliomas, lymphosarcomas or other malignant tumours, including so-called "solid" tumours.

In human therapy, they are thus used for the treatment of Hodgkin's disease and for other tumours which may benefit from treatment with vinblastine, vincristine or vindesine.

For use in therapy, the compounds according to the invention, if appropriate in lyophilised form, are preferably administered parenterally, in solution in a pharmaceutically acceptable solvent. Preferred addition salts are pharmaceutically acceptable non-toxic salts, such as salts of mineral acids, such as hydrochloric acid, phosphoric acid and sulphuric acid, or of organic acids, such as acetic acid, propionic acid, succinic acid, tartaric acid, oxalic acid, methanesulphonic acid or benzenesulphonic acid.

Physiological water or other saline solutions which are buffered, for example with a phosphate, are suitable solvents.

The active substance is in general administered in a dosage which can vary from 50 mg to several grammes.

The compounds according to the invention can also be used in combination with other anti-tumour agents.

EXAMPLE 18

(a) α and β isomers of 4-O deacetyl-4-O-L-N-acetylhemiaspartate vinblastine 250 mg of N-acetyl-L-asparatic anhydride are added to a solution of 700 mg (0.91 mmol) O-4 deacetylvinblastine in 20 ml anhydrous dicloromethane.

The solution is stirred during 20 hours at ambient temperature. After distillation under vacuum of the solvent, the obtained residue is purified by chromatography on silica (elution ether/methanol/NH$_4$OH 25% 60/49.75/0.25).

After trituration in a mixture of dichloromethane and petrol ether, 650 mg 4-O-deacetyl-4-O-L-N-acetylhemiaspartate vinblastine are obtained in the state of a white powder (Yield: 77%).

HPLC analysis of the product indicates the presence of both isomers α and β in a ratio of 85/15.

*IR spectrum (KBr): 3420, 2960, 2880, 1737, 1660, 1613, 1501, 1460, 1430 cm$^{-1}$.

*Mass spectrum: DCI (isobutane): 925 (M$^+$), 939 (M$^+$+14), 857, 769, 693, 635.

(b) α and β isomers of 4-O-deacetyl-4-O-L-N-acetylhemiaspartate methyl ester vinblastine A solution of 500 mg (0.540 mmoles) α and β isomers of 4-O-deacetyl-4-O-L-N-acetylhemiaspartate vinblastine in 10 ml absolute methanol saturated with dry HCl is stirred for 20 hours, at ambient temperature.

After distillation under vacuum of the solvent, the residue is recovered in a mixture of 15 ml distilled water and 15 ml dichloromethane. The mixture is rendered alkaline by NH$_4$OH addition. The aqueous phase is extracted by three portions of 20 ml dichloromethane. The organic extracts are combined, successively washed with 40 ml water and 40 ml of an aqueous solution saturated with NaCl, dried on magnesium sulfate and evaporated under reduced pressure. The residue is purified by chromatography on silica (elution by CH$_2$Cl$_2$:CH$_3$OH 95:5). Accordingly 410 mg α and β isomers of 4-O-deacetyl-4-O-L-N-acetylhemiaspartate methyl ester vinblastine are obtained, Yield: 81%.

Fractions resulting from chromatography including individual isomers are analyzed.

Principal isomer

*Mass spectrum (DCI, isobutane): 939 (M+), 940 (M++1), 953 (M++14);
*IR spectrum (KBr): 2950, 2880, 1740, 1675, 1615, 1503 cm$^{-1}$;
*NMR spectrum (CDCl$_3$, 360 MHz) δ: 9.65 (OH), 8.02 (NH), 7.52 (H-9'), 7.16–7.05 (H-10'; H-11', H-12'), 6.61 (H-9), 6.52 (NH), 6.07 (H-12), 5.75 (H-14), 5.52 (H-17), 5.17 (H-15), 4.75 (—C—NH), 3.95 (H-17A'), 3.80 (—OMe), 3.77 (—OMe), 3.70 (—OMe), 3.60 (—OMe), 2.80 (H-21A', H-21B'), 2.67 (NMe), 2.62 (H-21), 2.00 (MeCO), 0.92–0.75 (2 Me);
*Rf: 0.51 (CH$_2$Cl$_2$:CH$_3$OH 90:10 silica).

Minor Isomer

*Mass spectrum (DCI-isobutane): 939 (M+), 940 (M++1);
*IR Spectrum (KBr): 1740, 1675, 1615 cm$^{-1}$;
*NMR spectrum (CDCl$_3$, 360 MHz) δ: 9.25 (OH), 8.02 (NH), 7.50 (H-9'), 7.16–7.05 (H-10', H-11', H-12'), 6.75 (H-9), 6.52 (NH), 6.08 (H-12), 5.82 (H-14), 5.47 (H-17), 5.28 (H-15), 4.75 (CH—NHAc), 3.93 (H-17A'), 3.77 (2×OMe), 3.60 (OMe), 2.70 (N-Me), 2.02 (MeCo—), 0.95–0.77 (2 Me);
*Rf: 0.39 (CH$_2$Cl$_2$:CH$_3$OH 90:10 silica).

EXAMPLE 19

α and γ isomers of 4-O-deacetyl-4-O-L-N-carbobenzyloxyhemiglutamate vinblastine

A solution of O-4-deacetyl vinblastine (300 mg. 0.39 mmole) and N-carbobenzyloxy-L-glutamic anhydride (144 mg. 0.519 mmole) in dichloromethane (5 ml) is stirred for 20 hours, at ambient temperature.

The solvent is evaporated under vacuum.

The obtained residue is purified by chromatography on silica (elution: ether/methanol/NH$_4$OH 25% 50/49.5/0.5).

Accordingly, 230 mg of 4-O deacetyl-4-O-L-N-carbobenzyloxyhemiglutamate vinblastine are obtained in the state of an α and γ isomer mixture.

A HPLC analysis of the product indicates the presence of α and γ isomers in a ratio of 60:40.

IR spectrum (KBr): 3450, 2960, 2880, 1730, 1612, 1593, 1501, 1459, 1432, 1228 cm$^{-1}$;

Mass spectrum (DCI-isobutane): 1032 (M++1), 984, 928, 723 cm$^{-1}$.

EXAMPLE 20

Coupling of 4-O deacetyl-4-O-L-N-acetylhemiaspartate vinblastine with galactosylated albumin of human origin (a) 80,6 g of 4-O-deacetyl-4-O-L-N-acetylhemiaspartate vinblastine are dissolved in 2 ml dioxane. The solution is then plunged in a ice bath. 2.24 µl triethylamine in 0.5 ml dioxane and 22.6 ul isobutyl chloroformiate in 0.5 ml dioxane are added. The mixture is stirred for 1 hour.

Further, a solution of 200 mg galactosylated human albumin in 37 ml H$_2$O is prepared. The pH is adjusted to 8.5 by NaOH 0.1N.

The solution is refrigerated at 4 degrees C. After 1 hour, the activated ester is added to the solution of galactosylated human albumin. The solution is stirred for 14 hours at 4 degrees C., while the pH is maintained at 8.5 by addition of NaOH 1H. Thereafter, the solution is purified by filtration on a Sephadex gel G 25 equilibrated by a solution of NaCl 9/1000, pH=7.5. The fractions containing the conjugates are combined, concentrated by ultrafiltration and sterilized. The protein content is determined by the Lowry method and the content of alkaloids is estimated by determination of the radioactivity.

The obtained conjugate contains 13 moles of vinblastine per mole of galactosylated human albumin. The HPLC determination of monomers, dimers and polymers of the conjugate composition indicates 82% monomers and 18% dimers.

(b) 80,6 mg 4-O deacetyl-4-O-L-N-acetylhemiaspartate vinblastine are dissolved in 2 ml dioxane. The solution is then plunged in a ice bath. 24.4 µl triethylamine in 0.5 ml dioxane and 22.6 ul isobutyl chloroformiate in 0.5 ml dioxane are added.

Further, a solution of 200 mg of galactosylated human albumine in 37 ml phosphate buffer 0.1M, pH=8.2, is prepared. The pH is adjusted to 8.5 by NaOH 1N.

The solution is refrigerated at 4 degrees C. After 1 hour, the activated ester is added to the solution of galactosylated human albumin. The solution is stirred for 14 hours at 4 degrees C., while the pH is maintained at 8.5 by an addition of NaOH 1N. The solution is purified by filtration on Sephadex gel G25 equilibrated by a solution of NaCl 9/1000, pH=7.5. The fractions containing the conjugate are combined, concentrated by ultrafiltration and sterilized. The protein content of alkaloids is estimated by determination of the radioactivity.

The obtained conjugate contains 9.3 moles of vinblastine per mole galactosylated human albumin. The HPLC determination of monomers, dimers and polymers of the conjugate composition indicates 91.5% monomers, 7% dimers and 1.5% polymers.

The sensibility of the conjugate to lysosomial enzymes has been studied by incubation during 48 hours, at 37° C., in the presence of 5 mM cystein, 40 mM acetate buffer and lysosomial enzymes. Aliquot parts are taken and the non decomposed proteins are precipitated by addition of a trichloroacetic acid volume (TCA 40%). After incubation at 4° C., during one hour, said samples are centrifugated and the radioactivity of the supernatant is estimated by counting of scintillations of an aliquote part of the liquid.

The soluble radioactivity is a measure of the digestion of said conjugate. Practical tests has shown that 75% of the conjugate has been digested after 24 jours. No further evolution has been observed up to 48 hours.

The therapeutical activity of said conjugate has been estimated on P 388 Leucemia with female BDF$_1$ mices: $10^6$ tumoral cells are introperitoneally inoculated at the day 0. The conjugate is intraperitoneally administered at the day 1. The test results show that the conjugate presents an important activity on this experimental model, because it provides an increase in live time of more than 650% if it is administered at a rate of 60 mg/kg and the number of surviving mices is 5/5 after 60 days.

EXAMPLE 21

α and γ isomers of ethyl N-(4-O-deacetyl-4-O-L-N-acetylhemiaspartate-vinblastinoyl-23)-L-tryptophanate Following the procedure of example 18, ethyl N-(deacetyl-O-4-vinblastinoyl-23)-L-tryptophanate was converted to ethyl-N-(4-O-deacetyl-4-O-N-acetyl-hemiaspartate-vinblastinoyl-23)-tryptophanate (mixture of isomers α and γ).

The obtained residue is purified by chromatography on silica (elution ether/methanol/NH$_4$OH 25% 50/49.75/0.25).

200 mg of the product are obtained from 314 mg of starting ethyl N-(deacetyl-O-4-vinblastinoyl-23)-L-tryptophanate.

Mass spectrum (DCI, Acetone): 1126 ($M^{+1}$), 1066, 984, 970, 951, 911.

IR spectrum (KBr): 3400, 2960, 2940, 1740, 1665, 1618 cm$^{-1}$.

EXAMPLE 22

α and β isomers of ethyl N-(4-O-deacetyl-4-O-L-N-acetylhemiaspartate-vinblastinoyl-23)-L-isoleucinate Following the procedure of example 22, ethyl N-(deacetyl-O-4-vinblastinoyl-23)-L-isoleucinate was converted to ethyl-N-(4-O-deacetyl-4-O-L-N-acetyl hemiaspartate-vinblastinoyl23)-L-isoleucinate.

Mass spectrum (DCI-acetone): 1051 ($M^+$), 1036, 1009, 977, 897, 838, 755, 709, 652.

IR spectrum (KBr): 3410, 2963, 2929, 2880, 1734, 1676, 1612, 1500, 1460, 1430, 1372, 1333, 1293 cm$^{-1}$.

EXAMPLE 23

α and γ isomers of 4-O-deacetyl-4-O-L-N-acetylhemiglutamate vinblastine

Following the procedure of example 20, O-4-deacetylvinblastine was treated with N-acetyl-L-glutamic anhydride to yield 271 mg of O-4-deacetyl-4-O-L-N-acetyl-hemiglutamate vinblastine (mixture of isomers α and γ) from 380 mg of O-4-deacetylvinblastine.

Mass spectrum (DCl-acetone): 940 ($M^{+1}$), 871, 707.

IR spectrum (KBr): 3470, 2960, 2880, 1740, 1665, 1617 cm$^{-1}$.

What is claimed is:

1. Conjugate according to the formula:

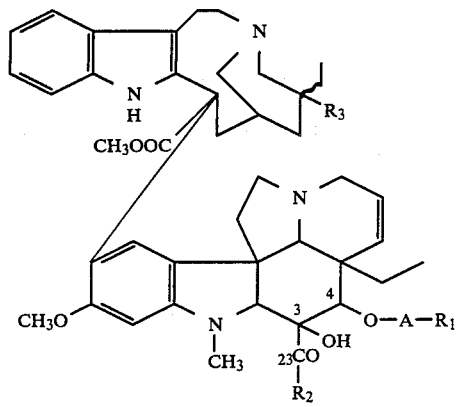

in which A represents an acetylamino-, trifluoroacetylamino- or carbobenzyloxyamino-substituted —CO(CH$_2$)$_n$CO— or

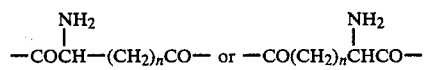

in which n varies from 1 to 5 R$_1$ represents a protein radical, R$_2$ represents a methoxy group, an amino group or an alpha aminoacid ester radical which is bonded by a bond of the amide type and in which the ester group contains 1 to 6 carbon atoms, and R$_3$ represents a hydrogen atom or a hydroxyl group, in each case in the two possible configurations, and its addition salts with an inorganic or organic acid.

2. Conjugate according to claim 1, in which A is

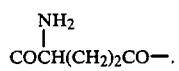

3. Conjugate according to claim 1, in which A is

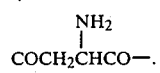

4. Conjugate according to claim 1 in which vinblastine or derivatives thereof is selected from the group consisting of vinblastine, vindesine or a vinblastin-23-oyl derivative of an aminoacid ester.

5. Conjugate according to claim 1, in which the protein radical is derived from fetuin or albumin.

6. Conjugate according to claim 1, in which the protein radical is derived from an immunoglobulin.

7. Conjugate according to claim 1, in which the protein radical is derived from a monoclonal antibody.

8. Conjugate according to claim 1, characterized in that the aminoacid ester is ethyl tryptophanate.

9. Conjugates according to claim 1, characterized in that the aminoacid ester is ethyl isoleucinate.

10. Conjugate according to claim 1, characterized in that R$_2$ represents a methoxy or amino group.

11. Product containing as a pharmaceutically active compound a conjugate in accordance with claim 1.

12. Product according to claim 11 wherein the active compound is contained under a lyophilised form.

13. Product according to claim 11 wherein the active compound is in solution in a buffered solvent.

14. Product according to claim 11 wherein A is

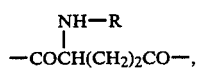
—COCH(CH₂)₂CO—,

R being acetyl, trifluoroacetyl or carbobenzyloxy.

15. Product according to claim 11 wherein A is

—COCH₂CHCO—,

R being acetyl, trifluoroacetyl or carbobenzyloxy.

16. Process for preparing a conjugate according to claim 1 comprising the steps of: condensing in a first stage a chloride or anhydride containing an A moiety onto the hydroxyl at C-4 of 4-O deacetylvinblastine or one of the derivatives of the 4-O-deacetylvinblastine-3-carboxamide type and by further condensing the thus obtained products with a protein in a solvent in which the compounds are soluble.

17. The process of claim 16 wherein said chloride or anhydride is an anhydride of aspartic or glutamic acid.

18. Process according to claim 16 in which the said solvent is a mixture of water and dioxane.

19. Process according to claim 16 wherein the conjugated product thus obtained is isolated by precipitation out of the reaction medium and is further centrifuged off, rinsed, lypholized and purified by gel filtration.

20. Process according to claim 16 wherein the protein employed has been galactosylated.

21. Conjugate according to claim 1 in which A is

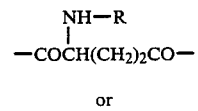
—COCH(CH₂)₂CO— or

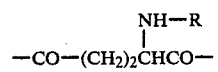
—CO—(CH₂)₂CHCO— in which R is acetyl or carbobenzyloxy.

* * * * *